United States Patent
Siegl et al.

(10) Patent No.: US 11,763,144 B2
(45) Date of Patent: Sep. 19, 2023

(54) VOLUME BASED PREDICTION OF PHYSICAL PROPERTIES IN SPORTS ARTICLES

(71) Applicant: adidas AG, Herzogenaurach (DE)

(72) Inventors: Christian Siegl, Zirndorf (DE); Jochen Suessmuth, Erlangen (DE); Jacques Perrault, Herzogenaurach (DE); Derek Luther, Lake Oswego, OR (US); Andrew Schneider, Portland, OR (US); Dustin Kendrick, Portland, OR (US); Mario Poerner, Erlangen (DE); Mark Henderson, Portland, OR (US)

(73) Assignee: adidas AG, Herzogenaurach (DE)

(*) Notice: Subject to any disclaimer, the term of this patent is extended or adjusted under 35 U.S.C. 154(b) by 672 days.

(21) Appl. No.: 16/684,700

(22) Filed: Nov. 15, 2019

(65) Prior Publication Data

US 2020/0167648 A1 May 28, 2020

(30) Foreign Application Priority Data

Nov. 27, 2018 (DE) .......................... 102018220367.9

(51) Int. Cl.
| | |
|---|---|
| *G06N 3/08* | (2023.01) |
| *G06T 7/11* | (2017.01) |
| *G06N 20/00* | (2019.01) |
| *A43B 13/00* | (2006.01) |
| *G06T 7/00* | (2017.01) |
| *G01N 33/00* | (2006.01) |

(52) U.S. Cl.
CPC .............. *G06N 3/08* (2013.01); *A43B 13/00* (2013.01); *G06N 20/00* (2019.01); *G06T 7/0004* (2013.01); *G06T 7/11* (2017.01); *G01N 2033/008* (2013.01)

(58) Field of Classification Search
CPC ........ G06N 3/08; G06N 20/00; G06N 3/0454; G06N 3/045; A43B 13/00; G06T 7/0004; G06T 7/11; G01N 2033/008; B33Y 50/00; G06F 2113/10; G06F 30/23; G06F 30/27
See application file for complete search history.

(56) References Cited

U.S. PATENT DOCUMENTS

| 2015/0217520 A1 | 8/2015 | Karpas et al. |
| 2015/0269282 A1* | 9/2015 | Nelaturi .................. G06F 30/00 700/98 |
| 2021/0276270 A1* | 9/2021 | Luan ..................... B29C 64/393 |

OTHER PUBLICATIONS

German Patent Application No. 102018220367.9, Office Action dated Aug. 26, 2020, 20 pages (machine English translation provided).

(Continued)

*Primary Examiner* — Michael E Teitelbaum
(74) *Attorney, Agent, or Firm* — Kilpatrick Townsend & Stockton LLP

(57) ABSTRACT

Described are methods of estimating a physical property associated with a region of a sports article. The method includes determining a plurality of structural features within the region, determining, for each structural feature, a feature value, mapping each feature value to a physical property, wherein the mapping is based on a machine learning algorithm from a limited plurality of samples, and wherein each sample associates a feature value with a value of the physical property, and using the mapping to estimate the physical property for the region.

25 Claims, 2 Drawing Sheets

(56) References Cited

OTHER PUBLICATIONS

European Patent Application No. 19210638.3, Extended European Search Report dated Apr. 23, 2020, 12 pages.
Gu et al., "Bioinspired Hierarchical Composite Design Using Machine Learning: Simulation, Additive Manufacturing, and Experiment", Materials Horizons, vol. 5, No. 5, Jul. 2018, pp. 1-14.
Koeppe et al., "Efficient Numerical Modeling of 3D-Printed Lattice-Cell Structures Using Neural Networks", Manufacturing Letters, vol. 15, Jan. 2018, 6 pages.
Tang et al., "Lattice Structure Design and Optimization With Additive Manufacturing Constraints", IEEE Transactions on Automation Science and Engineering, vol. 15, No. 4, Oct. 2018, pp. 1-17.
European Patent Application No. 19210638.3, Office Action dated Jun. 15, 2022, 7 pages.
Office Action, Chinese Patent Application No. 201911179819.8, dated Feb. 24, 2023, 15 pages.

\* cited by examiner

VOLUME BASED PREDICTION OF PHYSICAL PROPERTIES IN SPORTS ARTICLES

CROSS REFERENCE TO RELATED APPLICATION

This application is related to and claims priority benefits from German Patent Application No. DE 102018220367.9, filed on Nov. 27, 2018, entitled VOLUME BASED PREDICTION OF PHYSICAL PROPERTIES IN SPORTS ARTICLES ("the '367 application"). The '367 application is hereby incorporated herein in its entirety by this reference.

FIELD OF THE INVENTION

The present invention relates to a method of estimating a physical property associated with a region of a sports article and to a method of manufacturing at least a part of a sports article.

BACKGROUND

Modern production techniques like additive manufacturing (e.g. 3D-printing) and assembling of, possibly many, components by robots usually require a simulation of the manufacturing process before the process is actually performed. The aim of such a simulation is to verify that the manufacturing process is actually feasible in reality. For example, in 3D-printing a major problem is the printability of beam structures which may be impaired by deformation effects due to gravity.

Available tools for such simulation involve, for example, finite element methods (FEM). The physical properties analyzed in such simulations usually reflect the reaction of the product to the application of some force or torque. Examples include, but are not limited to, elasticity, stiffness, shearing resistance, bending stiffness and printability in case of 3D-printing.

However, even on modern computers, state-of-the art simulation techniques like FEM may require significant run-times, often in the order of several hours, which makes it very expensive. Also, as the results of such simulations are often used during a design process to verify a current design, the whole process is delayed and less responsive. The number of designs to be tried by a designer may be limited due to long simulation times.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a method of estimating a physical property associated with a region of sports article comprises the steps of determining a plurality of structural features within the region, determining, for each structural feature, a feature value, mapping each feature value to a physical, wherein the mapping is based on a machine learning algorithm from a limited plurality of samples, and wherein each sample associates a feature value with a value of the physical property, and using the mapping to estimate the physical property for the region.

In some embodiments, the region is divided into sub-regions. The region may be bounded by a hexahedron or the region may be bounded by a quadrilateral.

In some embodiments, the structural features are associated with sub-regions. The sub-regions may be voxels or pixels, which can subdivide the region. Each sub-region may be associated with a feature value for a structural feature within the sub-region. The feature value associated with the sub-region may depend on the amount of the material present in the sub-region.

In some embodiments, the mapping is based on a machine learning algorithm that was trained using the samples. The mapping may be based on an artificial neural network that was trained using the samples. The artificial neural network may be a convolutional neural network, CNN.

In some embodiments, the association between feature values with a value that is representative of the physical property may be obtained for each sample using a finite element method, FEM.

In some embodiments, the sports article may be a shoe and the regions may be located in the midsole of the shoe.

In further embodiments, the sports article is a shoe and the region is located in the upper of the shoe.

In some embodiments, the method further comprises the step of subdividing the region into voxels, wherein at least one structural feature is associated with each voxel.

The physical property may be any one of the printability, elasticity, stiffness, and shearing resistance of a structural feature within the region. The structural feature may be a beam that connects nodes.

In some embodiments, the method further comprises the step of subdividing the region into pixels, wherein at least one structural feature is associated with each pixel. The structural feature may be a patch of material to be attached to the upper of the shoe.

According to certain embodiments of the present invention, a method of manufacturing at least a part of a sports article comprises the steps of estimating a physical property associated with a plurality of regions of the part of the sports article, optimizing the physical property using the estimate and considering at least one structural constraint for the part of the sports article, and manufacturing the part of the sports article.

In some embodiments, the step of manufacturing comprises additive manufacturing. The step of manufacturing may comprise providing a blank and placing at least one path on the blank.

In some embodiments, a part of the sports article is manufactured according to the method. Moreover, the sports article may comprise a part manufactured by the method.

BRIEF DESCRIPTION OF THE DRAWINGS

In the following detailed description, embodiments of the invention are described referring to the following figures.

BRIEF DESCRIPTION

Figure 1:
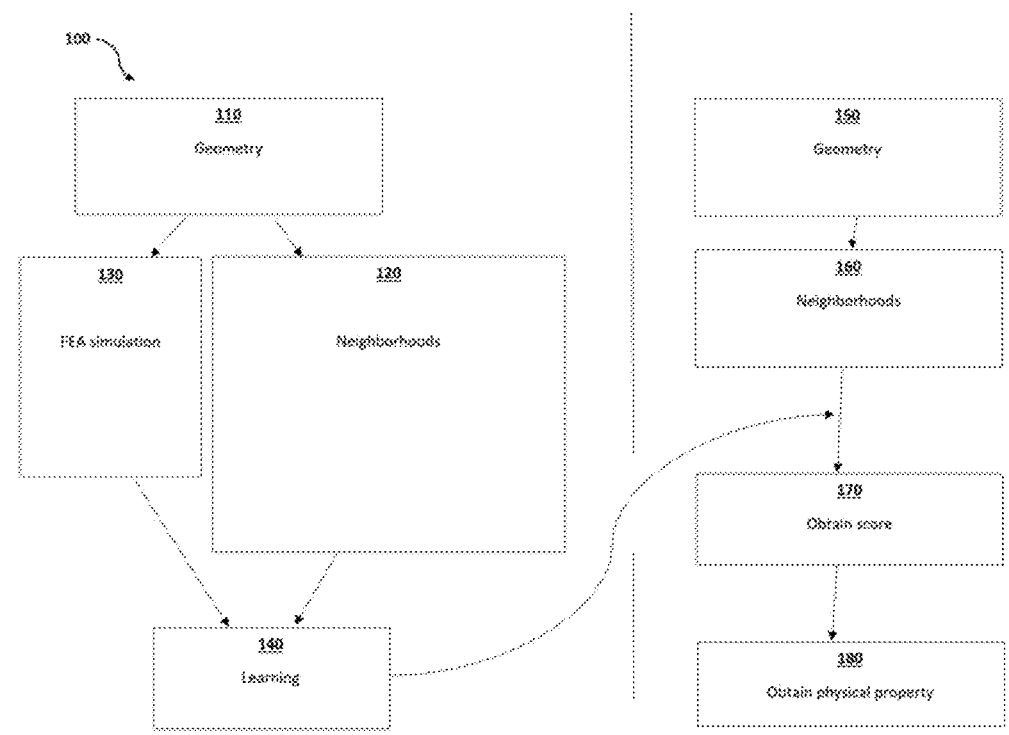
FIG. 1 is a flow chart illustrating an exemplary method according to certain embodiments of the present invention.

Therefore, it is the objective of the present invention to provide a method that significantly speeds up the simulation process of modern manufacturing techniques.

This objective is met by a method of estimating a physical property associated with a region of a sports article, comprising the steps: (a.) determining a plurality of structural features within the region; (b.) determining, for each structural feature, a value associated with the region; (c.) providing a mapping that maps the feature values to a value that is representative of the physical property, wherein the mapping is based on a plurality of samples, and wherein each sample associates feature values with a value of the physical property; and (d.) using the mapping to estimate the physical property.

In some embodiments, the method minimizes the need for costly and lengthy simulations to determine a physical property of a region of a sports article by estimating the physical property. One aspect that may be assessed by this technique is the producibility of a product. A good example is the producibility of a machined part on a milling machine. The producibility of the part depends on its complexity and if the milling machine offers the number and types of axis required. In the case of additive manufacturing, producibility effectively means printability. Whether a 3D geometry is printable on a certain printer may depend on the technology the printer uses for creating the geometry. One issue in 3D printing is the capability to print overhanging geometries. With a technology like selective laser sintering, where the part is printed within a powder, overhanging parts of geometry pose no challenge. Using other printing technologies like Fused Deposition Modeling or Stereolithography, the part is cured in free air or submerged within a liquid. In both cases, overhangs are may only be possible until a certain angle. After that, the geometry may deform or collapse. For parts exceeding this angle, either support structures have to be added or printing is no longer possible. There are a variety of parameters that vary with the print geometry and printer technology that all affect the producibility/printability of a given structure. Examples of other parameters that influence printability include, but are not limited to, the thickness of structures, print speed, resolution/detail and drainage (of powder, resin, etc.).

To characterize the region according, in some embodiments, a plurality of structural features within the region is determined. These features correspond to the material structure in the region and may, for example, describe the distribution of material in the region. A value may be determined for each of those structural features within the region. Thus, the values of the features may be characteristic for a particular region. As different regions typically have a different distribution of material, the corresponding structural feature values of each region may be different.

In the next step, a mapping may be used to estimate a value of the physical property. The mapping may be based on a plurality of samples, which had been obtained, for example, by a costly simulation that had been conducted before. For example, a FEM simulation might have been used to generate the samples. The samples associate (i.e. map) a particular feature value to the result of such a FEM simulation, for example, printability in the 3D-printing example mentioned above. The samples may then be used to obtain the mapping using, for example, a machine learning algorithm. Then a small number of remaining samples may be used to test the mapping.

In the final step, instead of using, for example, a costly FEM simulation, the mapping may be used to estimate the physical property. This may reduce the computation time significantly. Thus, the FEM simulation is run once for a particular sports article, but its results may be reused for different sports articles having a different structure.

The region may be divided into sub-regions. These sub-regions may correspond to neighborhoods of certain structural features. For example, in a midsole, the structural features may be beams and for a shoe upper they may be patches.

The region may be bounded by a hexahedron. A hexahedron is any polyhedron(i.e. three-dimensional geometrical shape) with six faces. It may be used, in the three-dimensional case, to subdivide a region in a regular or irregular manner.

The region may be bounded by a quadrilateral. A quadrilateral is a polygon (i.e. a two-dimensional geometrical shape) with four edges. It may be used, in the two-dimensional case, to subdivide a region in a regular or irregular manner.

The structural features may be associated with the sub-regions. A feature may be associated with each sub-region. In this way, a feature vector may be obtained, which is suitable to be fed, for example, into a neural network. Thus, the feature values associated with the sub-regions may yield a "fingerprint" of a particular region.

The sub-regions may be voxels or pixels which subdivide the region. Voxels refer to a three-dimensional volume, whereas pixels refer to a two-dimensional area. For example, in the case of a midsole to be 3D-printed, voxels may be used to subdivide the regions of the midsole. In the case of an upper on which patches are to be placed, pixels may be used to subdivide regions of the upper which in this case is regarded as a two-dimensional manifold.

Each sub-region may be associated with a feature value for a structural feature within the sub-region. The value associated with the sub-region may depend on the amount of material present in the sub-region. For example, the feature value for a particular sub-region may be a binary "1" if material is present in this sub-region, otherwise, it may be a binary "0". Thresholding may be used in the case of partial filling. For example, if there is 50% or more material present in a sub-region, the feature value may be a "1", otherwise the feature value may be "0". In this way, a feature vector may be obtained that corresponds to the structure of the region. In the example above, regions with different structures may be associated with different binary vectors.

The information contained in each sub-region (e.g. a pixel or voxel) may be binary as described previously. However, the information in each sub-region may also be on a grey-scale system to represent different amounts of material. Additionally, a third system entirely could be used in which a lot more detail is encoded into each sub-region. This may be particularly useful for lattices where the beams may be made of different materials or the same materials with different properties (e.g. caused by different curing), and also for patch arrangements on a lattice, where different materials, different orientations, and different built up layers could all be encoded into the voxel value. Therefore, the feature value associated with the sub-region may depend on the type of material present in the sub-region. Alternatively, the feature value associated with the sub-region may depend on the properties of the material present in the sub-region.

The greyscale system and the third system may both give a lot more detail to the information encoded, but the run times for these encoding systems could be longer. In some embodiments, when choosing what system would be most appropriate, the run times and the amount of information required must be balanced.

The mapping may be based on a machine learning algorithm that was trained using the samples. Machine learning comprises a vast spectrum of different algorithms, which aim to identify and exploit structures and patterns in data for inference and prediction. It may be beneficial for some algorithms are able to identify non-linear relationships between features and targets.

The mapping may be based on an artificial neural network that was trained using the samples. Artificial neural networks may comprise a number of neurons usually organized in layers. Each neuron in a particular layer may receive a weighted sum of the output of the cells of the previous layer. This sum is subject to a so-called activation function which usually is a non-linear function. The result of this function is the output of the neuron and is fed to the next layer. By stacking layers, the network is able to learn abstractions of the input data which might result in very precise predictions. Also, due to non-linear activation functions, a neural network may be able to identify non-linear relationships between features and targets.

The artificial neural network may be a convolutional neural network, CNN. In some embodiments, it may be desirable for the convolutional layers in a CNN to reduce the size of the features (e.g. number of pixels or voxels) by applying a convolution or cross correlation operation to its input. Thus, the number of free parameters (i.e. the weights of the network) may be significantly reduced resulting in a reduction in processing time. Also, such a network may be less prone to overfitting (i.e. learning "noise" in the data).

The association between feature values with a value that is representative of the physical property may be obtained for each sample using a finite element method ("FEM"). Generally, a FEM is able to provide rather precise estimates of physical properties and is a well-established method.

The sports article may be a shoe and the region may be located in the midsole of the shoe. The method according some embodiments may be suitable to predict physical properties such as the printability of a midsole by a 3D-printing process. Thus, instead of using costly FEM simulations, the method according to some embodiments, is able to predict the printability of a particular midsole design within seconds instead of hours. This speeds up the design process and allows a designer to try more design options. Moreover, it may provide feedback about the feasibility of the design more quickly.

The method may further comprise the step of subdividing the region into voxels, wherein at least one structural feature is associated with each voxel. Generally, a voxel represents a value on a grid in three-dimensional space. The value is characteristic of the structural feature.

The physical property may be one of printability, elasticity, stiffness and shearing resistance of a structural feature within the region. As mentioned, usually a full finite element analysis ("FEA") based on a FEM is conducted to explore whether a desired design is 3D-printable or to estimate elasticity, stiffness or shearing resistance. The present invention, therefore, provides a shortcut to this time-consuming and expensive approach by estimating the printability and/or other physical properties based on the samples of at least one past FEAs.

The structure may be a beam that connects nodes. For example, and as will be described in more detail herein, a midsole of a sports shoe may be made from a 3D-printed lattice of cells. Each cell may comprise beams that connect nodes. The nodes may be located at the faces of the cells.

The sports article may be a shoe and the region may be located in the upper of the shoe. In some embodiments, the method may also be used in a two-dimensional case, for example, to predict the physical properties of a shoe upper onto which patches are placed. Exemplary physical properties include, but are not limited to, bending stiffness and elasticity. In some embodiments, the physical property is the bending stiffness.

The method may further comprise the step of subdividing the region into pixels, wherein at least one structural feature is associated with each pixel. The value of each structural feature may depend on whether a patch is present in the pixel or not. In this way, the resulting feature vector represents the presence of patches in the particular region. As the patches influence the local properties of the upper, such as bending stiffness and elasticity, there may be a close correspondence between the feature vectors and the physical properties to be estimated.

The structural feature may be a patch of material to be attached to the upper of the shoe. Patches may provide the shoe upper with specific functions in certain areas. In some embodiments, the method estimates such functions without the need for time-consuming FEAs. For example, the stiffness provided to a shoe upper may be quickly estimated depending on the number, shape, and location of patches.

In some embodiments, the method includes manufacturing at least a part of a sports article, comprising the steps: (a.) estimating a physical property associated with a plurality of regions of the part of the sports article as described herein; (b.) optimizing the physical property using the estimate and considering at least one structural constraint for the part of the sports article; and (c.) manufacturing the part of the sports article.

The structural constraints may, for example, be set by a designer and may, for example, relate to aesthetical aspects of the design. In another example, the constraint may be more of a technical nature and may, for example, refer to a minimum bending stiffness. The method may be used to obtain an optimal design respecting the constraint very quickly because time-consuming and expensive simulations may be avoided in the optimization loop. Instead, in some embodiments, the physical property to be optimized may be estimated by samples using the method.

The step of manufacturing may comprise additive manufacturing. In some embodiments, the method may be applied to simulating an additive manufacturing process, such as a 3D-printing process, and may yield a significant speedup compared to conventional full FEM simulations.

The step of manufacturing may comprise: providing a blank; and placing at least one patch on the blank. Such a patch-placement process may be used to manufacture a shoe upper. Again, in some embodiments, the method may speed up the whole process also in this two-dimensional case.

Another aspect of the present invention, in some embodiments, relates to a part of a sports article which is manufactured according to the method of manufacturing described above. Another aspect of the present invention, in some embodiments, relates to a sports article comprising such part.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

In the following, only some possible embodiments of the invention are described in detail. It is to be understood that these exemplary embodiments may be modified in a number of ways and combined with each other whenever compatible and that certain features may be omitted in so far as they appear dispensable.

FIG. 1 shows a flow chart of an exemplary method 100, according to some embodiments, with respect to the designing and/or manufacture of a midsole for a sports shoe by a 3D-printing process. It is to be understood that the present invention is neither limited to the manufacture of shoes nor to the usage of a particular manufacturing process.

The method, according to the invention, is based on the idea of looking at volumetric neighborhoods around structure elements. In some embodiments, these structure elements are beams inside a lattice structure. It was noted that these volumetric neighborhoods have a direct relationship to the printability of that element, since it covers both, the element itself and the network effect with the surrounding. This volume-based method of linking a local neighborhood to physical properties may be used for a number of physical parameters such as, for example, bending stiffness, shearing stiffness, etc. Basically, all physical or production parameters may be estimated with the method described herein.

Generally, the left side of FIG. 1 shows the learning process (i.e. establishing the relationship between the structure of the sole and the physical property) as well as the printability in the according to some embodiments. The right side of FIG. 1 shows how the learned relationship may be used to make predictions or inferences based on the learned relationship.

In some embodiments relating to 3D-printing a midsole of a sports shoe, the target property to be estimated may be the printability of the midsole. Thus, in a first step 110, the geometry of the midsole is provided. This geometry may be provided by a designer. Alternatively, the geometry may be the result or intermediary result of an automated design process that aims to optimize certain objectives functions, such as, for example, bending stiffness given a number of constraints, which may be provided by a designer. In any case, a region is identified in step 110 with a geometry made up of structural features.

For a midsole, the structural features may be beams. However, for an upper the structural features may be patches.

The printability of a lattice structure is an important aspect of the producibility and production speed of 3D-printed midsoles. The actual boundary conditions and speed may highly depend on the printer and printing technology. Examples of such boundary conditions include, but are not limited to, struts that are not allowed to be narrower than 0.7 mm, overhanging structures without support, and an angle relative to the print platform that should not be below 45 degrees. Those constraints generally depend on the local neighborhood and the print speed. As a rule of thumb, the quicker the printing process, the stricter those constraints may have to be met—otherwise printing may fail.

In step 120, according to some embodiments of the exemplary method 100, the region is broken up into neighborhoods, wherein each neighborhood is centered on a structural feature—the window size of the neighborhood may be chosen to be narrowly focused on the structural feature or wider to incorporate more of the neighborhood. The neighborhoods may then be subdivided into voxel elements. Generally, a voxel represents a value on a grid in three-dimensional space. For every beam of the midsole, a voxel volume (also denoted as a "window" or a bounding region), may be created around a center or around a different point of interest. This step may require some parameters to be fixed beforehand, like, for example, the size of the voxels (window size), the resolution and whether a signed distance field, or a binary volume is used. For example, depending on the globality of the physical properties, different window sizes may be selected. The voxel size (or pixel size in the two-dimensional case) may be dictated by the window size and the resolution.

In some embodiments, in step 120, a feature value may be obtained from the signature of the structural feature(e.g. a beam of a cell of midsole). More precisely, a vector of feature values may be obtained from the representation of the structural feature by the voxels (or pixels in the two-dimensional case).

Figure 2A:
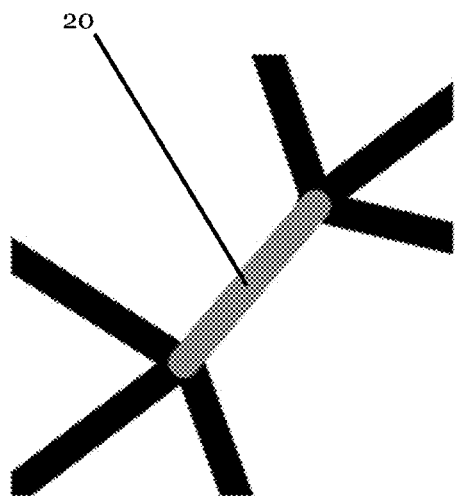
FIG. 2A is a beam of a cell of a lattice structure according to certain embodiments of the present invention.
Figure 2B:
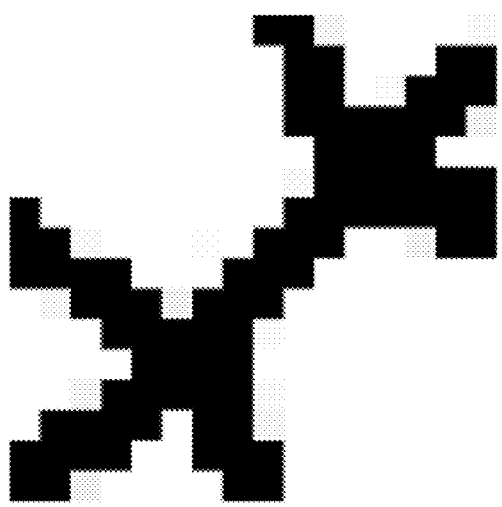
FIG. 2B is a voxelated region of the beam of FIG. 2A.

FIG. 2A shows an exemplary beam of a cell of a lattice structure that may be part of a midsole to be 3D-printed. In FIG. 2B, the corresponding voxelated region of the beam is shown, wherein a voxel is black (i.e. a binary "1") if there is material present in the corresponding voxel or white(i.e. a binary "0") otherwise. In the example, a 16×16×16 binary signature of the beam is obtained which can then be linearized into a binary feature vector of size 4096.

In step 130 of the exemplary method 100 a high fidelity FEA based printability analysis for the full midsoles is run. The result of this analysis is deformation information that happens during printing. This deformation may be directly linked to printability as large deformation leads to problems during printing. By linking this information back to the beam for which it was computed the required training data for the subsequent estimation of printability may be obtained. More precisely, the FEA simulation provides a score for each structural feature. A score is a value that represents the physical property being investigated—e.g. tearing resistance, printability etc. Thus, the relationship between the result of the FEA (i.e. the score) and the corresponding element may be established in step 130.

In step 140, a relationship between the feature vector of each element and the associated physical property of the element (i.e. the score as obtained by the FEA simulation) may be learned. Thus, the voxelated elements may form a limited plurality of samples to a machine learning algorithm. For example, a standard machine learning algorithm, namely a convolutional neural network (CNN) may be used. This network may be trained to learn the relationship between voxel based neighborhoods and the corresponding physical properties (i.e. printability). The result of this step is a mapping that directly translates feature vectors (here voxel volumes) into physical properties (here printability) without the detour over a costly FEA system.

So far, steps 110-140 of the exemplary method 100 relate to the learning side of the method. The result of these steps is a trained neural network with a set of weights corresponding to the "strength" of connections between the neurons of the network. The further steps of the method relate to applying the learned relationships beam structure/beam neighborhood and printability to a previously unknown midsole structure obtained in step 150, which is similar to step 110 of the learning phase. The phase illustrated on the right side of FIG. 1 is also referred to as the prediction phase and corresponds to the method steps of claim 1.

In this phase, a printability score for every beam needs to be obtained quickly. To achieve this, a neighborhood may be established around beams of the geometry obtained in step 150. In addition, the neighborhood may be voxelated in step 160 following the same rules that were used during training (i.e. in step 120). In the same step, feature vectors may be obtained for each beam, as was described with respect to the learning phase. In step 170 the feature vectors may be fed into the neural network that was trained in the training phase to finally obtain a printability score associated with the corresponding beam. Finally, in step 180 all scores for all structural features in the region of the midsole may be used to obtain a value for the physical property for the whole region(e.g. printability).

Thus, the printability of the new midsole design may be obtained without using a full FEA simulation. The prediction phase of the neural network is finished in the order of a few seconds compared to the FEA runtime of several hours.

In some embodiments, the method may not only be used in the context of 3D-printing and for predicting printability based on local neighborhoods. Rather, arbitrary physical properties may be quickly estimated using the method.

In some embodiments, the method may relate to the placement of reinforcement patches on a shoe upper. Even with a low number of patches and materials, a huge number of configurations may be possible. Usually, every combination has to run through expensive FEA simulations. For every target parameter, such as. roll-over stiffness, homogenous pressure, etc., a separate FEA run may be required. Looking at customer-specific on-demand production, this is not viable, as simulation alone would run several hours. In addition, this traditional approach comes at high costs both in terms of the FEA software and computational power.

To overcome these disadvantages, the same approach as described above may be used. The only difference is, that the method is performed in 2D instead of 3D. Looking at a flat representation of the shoe upper, every pixel is supposed to represent the combined material stiffness at this position. With this input, convolutional neuronal networks (CNN) may be used to link this information to results from a FEA. For every target like for example roll-over stiffness, homogenous pressure, etc., a separate CNN may be trained.

In the following, further examples are described to facilitate the understanding of the invention:

1. A method of estimating a physical property associated with a region of sports article comprising, the steps:
   a. determining a plurality of structural features within the region;
   b. determining, for each structural feature, a feature value;
   c. mapping each feature value to a physical property, wherein the mapping is based on a machine learning algorithm from a limited plurality of samples, wherein each sample associates a feature value with a value of the physical property; and
   d. using the mapping to estimate the physical property for the region.
2. Method according to example 1, wherein the region is divided into sub-regions.
3. Method according to one of examples 1-2, wherein the region is bounded by a hexahedron.
4. Method according to one of examples 1-3, wherein the region is bounded by a quadrilateral.
5. Method according to one of examples 2-4, wherein the structural features are associated with the sub-regions.
6. Method according to one of examples 2-5, wherein the sub-regions are voxels or pixels which subdivide the region.
7. Method according to one of examples 2-6, wherein each sub-region is associated with a feature value for a structural feature within the sub-region.
8. Method according to example 7, wherein the feature value associated with the sub-region depends on the amount of material present in the sub-region.
9. Method according to one of examples 1-8, wherein the mapping is based on a machine learning algorithm that was trained using the samples.
10. Method according to one of examples 1-9, wherein the mapping is based on an artificial neural network that was trained using the samples.
11. Method according to one of examples 1-10, wherein the artificial neural network is a convolutional neural network, CNN.
12. Method according to one of examples 1-11, wherein the association between feature values with a value that is representative of the physical property is obtained for each sample using a finite element method, FEM.
13. Method according to one of examples 1-11, wherein the sports article is a shoe and the region is located in the midsole of the shoe.
14. Method according to example 13, further comprising the step of subdividing the region into voxels, wherein at least one structural feature is associated with each voxel.
15. Method according to one of examples 1-14, wherein the physical property is any one of the printability, elasticity, stiffness and shearing resistance of a structural feature within the region.
16. Method according to example 15, wherein the structural feature is a beam that connects nodes.
17. Method according to one of examples 1-11, wherein the sports article is a shoe and the region is located in the upper of the shoe.
18. Method according to example 17, further comprising the step of subdividing the region into pixels, wherein at least one structural feature is associated with each pixel.
19. Method according to examples 17-18, wherein the structural feature is a patch of material to be attached to the upper of the shoe.
20. A method of manufacturing at least a part of a sports article, comprising the steps:
   a. estimating a physical property associated with a plurality of regions of the part of the sports article to one of examples 1-19;
   b. optimizing the physical property using the estimate and considering at least one structural constraint for the part of the sports article; and
   c. manufacturing the part of the sports article.
21. Method according to example 20, wherein the step of manufacturing comprises additive manufacturing.
22. Method according to example 20, wherein the step of manufacturing comprises:
   providing a blank;
   placing at least one patch on the blank.
23. A part of a sports article which is manufactured according to a method of one of examples 20-22.
24. A Sports article comprising a part according to example 23.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of estimating a physical property associated with a region of sports article comprising, the steps:
   determining a plurality of structural features within the region, wherein each structural feature of the plurality of structural features comprises a distribution of a material within the region;
   determining, for each structural feature, a feature value of the distribution of the material within the region;
   mapping each feature value to a physical property, wherein the mapping is based on a machine learning algorithm from a limited plurality of samples, wherein each sample associates a feature value with a value of the physical property, and wherein the physical property comprises printability of the structural feature; and
   using the mapping to estimate the physical property for the region.

2. The method of claim 1, wherein the region is divided into sub-regions.

3. The method of claim 1, wherein the region is bounded by a hexahedron.

4. The method of claim 1, wherein the region is bounded by a quadrilateral.

5. The method of claim 2, wherein the structural features are associated with the sub-regions.

6. The method of claim 2, wherein the sub-regions are voxels or pixels which subdivide the region.

7. The method of claim 2, wherein each sub-region is associated with a feature value for a structural feature within the sub-region.

8. The method of claim 7, wherein the feature value associated with the sub-region depends on an amount of material present in the sub-region.

9. The method of claim 1, wherein the mapping is based on a machine learning algorithm that was trained using the plurality of samples.

10. The method of claim 1, wherein the mapping is based on an artificial neural network that was trained using the plurality of samples.

11. The method of claim 10, wherein the artificial neural network is a convolutional neural network.

12. The method of claim 1, wherein an association between the feature value with a value that is representative of the physical property is obtained for each sample using a finite element method.

13. The method of claim 1, wherein the sports article is a shoe and the region is located in a midsole of the shoe.

14. The method of claim 13, further comprising a step of subdividing the region into voxels, wherein at least one of the plurality of structural features is associated with each voxel.

15. The method of claim 1, wherein the physical property further comprises any one of elasticity, stiffness, and shearing resistance of the structural feature within the region.

16. The method of claim 15, wherein the structural feature is a beam that connects nodes.

17. The method of claim 1, wherein the sports article is a shoe and the region is located in an upper of the shoe.

18. The method of claim 17, further comprising a step of subdividing the region into pixels, wherein at least one of the plurality of structural features is associated with each pixel.

19. The method of claim 17, wherein the structural feature is a patch of material to be attached to the upper of the shoe.

20. A method of manufacturing at least a part of a sports article, comprising the steps:
   a. estimating the physical property associated with a plurality of regions of a part of the sports article according to claim 1;
   b. optimizing the physical property using the estimate and considering at least one structural constraint for the part of the sports article; and
   c. manufacturing the part of the sports article.

21. The method of claim 20, wherein the step of manufacturing comprises additive manufacturing.

22. The method of claim 20, wherein the step of manufacturing comprises:
   providing a blank; and
   placing at least one patch on the blank.

23. A part of a sports article which is manufactured according to a method of claim 20.

24. A Sports article comprising a part according to claim 23.

25. A method of manufacturing at least a part of a sports article, comprising:
   a. estimating a physical property associated with each of a plurality of regions of a part of the sports article according to a process that includes, for each region of the plurality of regions:
      (i) determining a plurality of structural features within the region, wherein each structural feature of the plurality of structural features comprises a distribution of a material within the region;
      (ii) determining, for each structural feature, a feature value of the distribution of the material within the region;
      (iii) mapping each feature value to a physical property, wherein the mapping is based on a machine learning algorithm from a limited plurality of samples, wherein the mapping is based on a machine learning algorithm that was trained using the plurality of samples, wherein each sample associates a feature value with a value of the physical property, and wherein the physical property comprises printability of the structural feature; and
      (iv) using the mapping to estimate the physical property for the region, wherein the sports article is a shoe and the region is located in a midsole of the shoe;
   b. optimizing the physical property using the estimate and considering at least one structural constraint for the part of the sports article; and
   c. manufacturing the part of the sports article.

* * * * *